United States Patent [19]

Sugier et al.

[11] 4,291,126

[45] Sep. 22, 1981

[54] PROCESS FOR MANUFACTURING ALCOHOLS AND MORE PARTICULARLY SATURATED LINEAR PRIMARY ALCOHOLS FROM SYNTHESIS GAS

[75] Inventors: André Sugier; Edouard Freund, both of Rueil-Malmaison, France

[73] Assignee: Institut Francais du Petrole, Rueil-Malmaison, France

[21] Appl. No.: 105,312

[22] Filed: Dec. 19, 1979

[30] Foreign Application Priority Data

Dec. 19, 1978 [FR] France ................................. 78 35870

[51] Int. Cl.$^3$ ............................................. C07C 27/06
[52] U.S. Cl. .................................... 518/713; 252/462
[58] Field of Search ...................... 260/449.5, 449.6 R

[56] References Cited

U.S. PATENT DOCUMENTS

| | | | |
|---|---|---|---|
| 1,920,373 | 8/1933 | Gosselin | 260/449.6 X |
| 2,517,035 | 8/1950 | Sensel et al. | 260/449.6 R |
| 2,960,518 | 11/1960 | Peters | 260/449.6 |
| 4,122,110 | 10/1978 | Sugier et al. | 210/449.5 |

FOREIGN PATENT DOCUMENTS

| | | | |
|---|---|---|---|
| 530932 | 9/1956 | Canada | 260/449.6 |
| 1092458 | 11/1960 | Fed. Rep. of Germany | 260/449.6 |

*Primary Examiner*—Howard T. Mars
*Attorney, Agent, or Firm*—Millen & White

[57] ABSTRACT

Process for manufacturing alcohols by reaction of carbon monoxide with hydrogen in the presence of a catalyst containing from 20 to 60% of copper, from 5 to 50% of cobalt, from 5 to 30% of a metal selected from chromium, iron, vanadium and manganese, from 5 to 40% of a rare earth metal, from 0.1 to 5% of an alkali or earth-alkali metal and, optionally, zinc and/or a noble metal from group VIII and/or a binder selected from alumina, magnesia and cements.

26 Claims, No Drawings

PROCESS FOR MANUFACTURING ALCOHOLS AND MORE PARTICULARLY SATURATED LINEAR PRIMARY ALCOHOLS FROM SYNTHESIS GAS

BACKGROUND OF THE INVENTION

This invention concerns a catalytic process for the synthesis of saturated linear primary alcohols from carbon monoxide and hydrogen.

French Pat. No. 2,369,234 (EN 76 33046), corresponding to U.S. Pat. No. 4,122,110, discloses the use of particular catalysts for carrying out the process of manufacturing linear saturated primary alcohols from CO, $H_2$ or CO, $CO_2$, $H_2$ mixtures and having, with respect to the above mentioned process, the following advantages:

an excellent selectivity to alcohols, often higher than 95%;

a selectivity to linear saturated primary alcohols having 2 or more carbon atoms, which is often higher than 70% by weight;

a high yield, in most cases higher than 100 kg of $C_2^+$ alcohols per ton of catalyst and per hour.

It has now been found that it is possible to further increase the yield of $C_2^+$ alcohols, whose commercial value is higher than that of methanol and which, moreover, are much more compatible with the motor fuels and favor, by their presence, the addition of substantial amounts of methanol to gasolines.

DETAILED DISCUSSION

This result is obtained by making use of a catalyst containing at least 5 essential elements, i.e. copper, cobalt, a third metal M selected from chromium, iron, vanadium and manganese, a fourth metal which is a rare earth metal N and a fifth metal which is an alkali metal A, preferably lithium, sodium or potassium or an alkali-earth metal, preferably calcium or barium. Optionally zinc may also be present. These elements are used in the following proportions (% by weight of metal with respect to the total of the metals):

copper: from 20 to 60% and preferably from 25 to 50%,
cobalt: from 5 to 50% and preferably from 10 to 40%,
metal M: from 5 to 30% and preferably from 10 to 25%,
metal N: from 5 to 40% and preferably from 10 to 30%,
metal A: from 0.1 to 5% and preferably from 0.2 to 3%.

The above proportions being relative metal contents, do not indicate the precise form in which the metal is present, this form being not necessarily the same during the reaction as in the fresh catalyst.

When zinc is present, it is used in a proportion of from 0.5 to 15% of the total metal weight.

The metals Cu, Co, M, N and optionally Zn are used generally as oxides such as CuO, CoO, $Cr_2O_3$, $La_2O_3$ or salts decomposable by heat such as carbonates, sulfates, nitrates, oxalates, tartrates, citrates, acetates, succinates or, even, as complexes, for example a chromate or a vanadate.

The metal A may be introduced together with the other metals, as a salt or hydroxide, or subsequently to the powder or to the catalyst already formed. Examples of such salts are the nitrate, the acetate, the tartrate and the carbonate of calcium, barium, sodium or potassium, preferably of potassium.

An improvement of the invention consists of adding a sixth element to the catalyst in the form of at least one noble metal from group VIII, for example platinum, palladium, iridium or rhodium. The relative content of this metal is, for example, from 0.005 to 0.5%, preferably from 0.02 to 0.1%. As a matter of fact there is observed, in this case, an improvement in the production of alcohols with a simultaneous reduction of the undesirable formation of dimethyl ether.

For the preparation of these catalyst masses, it is preferable to make use of preparation techniques adapted to obtain a product whose composition is as homogeneous as possible and to avoid the segregation of the different elements during the preparation. There can be used particularly the coprecipitation techniques and techniques of preparation making use of thickening agents such as gums. There can be added binders, for example alumina, magnesia or a cement. For example, the alumina may be in a proportion from 0 to 25%, preferably 1 to 25%, calculated as aluminum, with respect to the weight of the catalyst composition.

The preparation method for producing the catalysts having the higher selectivity, and which is accordingly preferred, consists of preparing a common solution of the compounds of the metals Cu, Co, M and N, by adding an agent selected from the complexant organic compounds, preferably selected from:

the organic acids containing two or more acid groups, for example the oxalic, malonic, succinic or glutaric acids, the alcohol-acids, for example glycolic, lactic, malic, tartaric or citric acids, the amino-acids, for example aminoacetic acid, alanine or leucine.

Water is evaporated from the resultant solution, for example by heating at a temperature from 200° to 600° C., so as to obtain a powder which is agglomerated, preferably by means of an aluminous cement containing aluminum and lime as calcium aluminate.

The shaping may be performed according to the conventional techniques of the art and particularly by pelletizing or by extrusion; it can also be performed by bowl granulation, particularly by adding refractory aluminous cements which, in addition to their binding action, have a catalytic activity due to their basicity. The preferred aluminous cements contain 40 to 85% by weight of $Al_2O_3$ and 15 to 30% of CaO with, optionally, small amounts of other components. Alumina and lime are present in major part as calcium aluminates.

Generally, the operation is completed by drying and roasting, for example at a temperature of about 300°–800° C. The incorporation of one or more alkali metals may be performed before or after the shaping of the catalyst, for example by impregnation with a solution of soluble salts or hydroxides of one or more alkali metals. This addition may also be conducted, before the drying and roasting step, by addition of a solution containing one or more soluble compounds of alkali metals; it may also be performed with chromates or dichromates of one or more alkali metals.

The conditions of use of these catalysts, for the manufacture of alcohols, are usually as follows: the pressure is generally comprised between 20 and 250 bars, preferably between 50 and 150 bars, the ratio $H_2/CO$, $CO_2$ being advantageously from 0.4 to 10, but preferably from 0.5 to 4 and the temperature being in the range from 150° to 400° C., but preferably from 220° to 350° C.

CATALYST A (reference catalyst)

To a mixture of 160 g of chromic anhydride $CrO_3$, 483 g of copper nitrate $Cu(NO_3)_2$, $3 H_2O$ and 233 g of cobalt carbonate $2 CoCO_3$, $3 Co(OH)_2$, n $H_2O$ having a cobalt content of 50.5% by weight, there is added 450 ml of water and then, after the end of the gas evolution, 100 g of citric acid. There is thus obtained a solution which is evaporated and dried for 2 hours at 200° C., then heated in air for 3 hours at 450° C.

One half of the resultant powder, having the molar composition $(Cr_2O_3)_{0.4}$, $(CuO)_1$, $(CoO)_1$ is pelletized to pellets of 5×5 mm. These pellets are then impregnated with a potassium hydroxide solution so as to deposit potassium in a proportion of 2% by weight, expressed as $K_2O$. By heating for 2 hours at 400° C. in air, there is thus obtained catalyst $B_1$ where the metals are present in the following relative proportions in % by weight:

Cu=37.9   Co=35.2   Cr=24.8   K=2.1 and by moles: $Cu_1 Co_1 Cr_{0.8} K_{0.09}$

CATALYSTS D, E, F (reference catalysts)

To 9 liters of an aqueous solution, brought to 60° C., of 16 moles of sodium carbonate, there is quickly added 6 liters of an aqueous solution containing 6 moles of copper nitrate and 6 moles of cobalt nitrate. The resulting precipitate is settled, washed and dried at 200° C. The resulting powder is divided in three equal parts.

CATALYST D

⅓ of the powder is impregnated with a solution containing 1.6 mole of manganese nitrate and then dried at 200° C. and treated for 2 hours at 450° C. The resulting powder is pelletized to pellets of 5×5 mm which are impregnated with a potassium hydroxide solution so as to deposit thereon 2% by weight of $K_2O$. After treatment for 2 hours at 400° C., catalyst D is obtained where the metals are present in the following molar proportions:

Cu Co $Mn_{0.8} K_{0.12}$.

CATALYST E

⅓ of the powder is impregnated with a solution containing 1.6 mole of iron nitrate, then dried at 200° C. and heated in air for 2 hours at 450° C. The resulting powder is pelletized and then impregnated with potassium hydroxide and thermally treated as catalyst D. There is so obtained catalyst E having the molar composition:

Cu Co $Fe_{0.8} K_{0.12}$.

CATALYST F

The last third of the powder is impregnated with a solution containing 1.6 mole of ammonium vanadate and then dried at 200° C. The resulting powder is shaped, impregnated with potassium hydroxide and thermally treated as catalysts D and E, whereby catalyst F is obtained, whose molar composition is:

Cu Co $V_{0.8} K_{0.12}$.

CATALYSTS $B_1$ and $B_2$

To a solution in 500 ml of water of 100 g of chromic anhydride $CrO_3$, 260 g of lanthanum nitrate $La(NO_3)_3$, $6 H_2O$, 483 g of copper nitrate $Cu(NO_3)_2$, $3 H_2O$ and 582 g of cobalt nitrate $Co(NO_3)_2$, $6 H_2O$, there is added 100 g of citric acid. The obtained solution is evaporated, under dry conditions, for 2 hours at 200° C., then heated in air for 3 hours at 400° C. The resulting powder is pelletized to pellets of 5×5 mm.

The results pellets are impregnated with a potassium hydroxide solution so as to deposit potassium in a proportion, expressed as $K_2O$, of 2% by weight. One half of the pellets is heated for 2 hours at 400° C. in air. There is thus obtained catalyst $B_1$ where the metals are present in the following relative proportions: (in % by weight)

Cu=32.8   Co=30.5   Cr=13.4   La=21.5   K=1.8 and by moles: $Cu_1 Co_1 Cr_{0.5} La_{0.3} K_{0.09}$.

The second half of the pellets is heated for 2 hours at 400° C. in air and then impregnated with a solution of chloroplatinic acid so as to deposit 500 ppm by weight of platinum.

There is thus obtained catalyst $B_2$ whose relative composition is the same except that it further contains 0.05% of platinum.

CATALYST C

The operation is the same as for catalyst $B_1$, except that the 260 g of lanthanum nitrate are replaced by 260 g of cerium nitrate $Ce(NO_3)_3$, $6 H_2O$.

The resultant catalyst has the following relative composition (in % by weight):

Cu=32.8   Co=30.4   Cr=13.4   Ce=21.6   K=1.8 and by moles: $Cu_1$   $Co_1$   $Cr_{0.5}$   $Ce_{0.3}$   $K_{0.09}$.

CATALYSTS $D_1$, $D_2$ and $E_1 F_1$

To 9 liters of an aqueous solution, brought to 60° C., of 16 moles of sodium carbonate, there is rapidly added 6 liters of an aqueous solution containing 6 moles of copper nitrate and 6 moles of cobalt nitrate. The resulting precipitate is settled, washed to remove the sodium and dried at 200° C. The resulting powder is divided in three equal parts.

CATALYSTS $D_1$ AND $D_2$

⅓ of the powder is impregnated with a solution containing 1 mole of manganese nitrate and 0.6 mole of didymium carbonate, having a 70% by mole content of neodymium and 30% by mole of praseodymium, dissolved with 100 ml of concentrated nitric acid. After impregnation, the reaction is continued for 2 hours and the resulting product is then dried at 200° C. for 4 hours and heated for 2 hours at 400° C. in the presence of air.

The resulting powder is pelletized to pellets of 5×5 mm which are impregnated with a potassium hydroxide solution so as to deposit 1.8% by weight of potassium expressed as $K_2O$.

After heating in air for 2 hours at 400° C., there is obtained catalyst $D_1$ wherein the metals are present in the following relative proportions in % by weight:

Cu=32.3,   Co=30,   Mn=14,   didymium=21.8,   K=1.8, and by moles: $Cu_1$   $Co_1$   $Mn_{0.5}$   $Nd_{0.21}$   $Pr_{0.09}$ $K_{0.09}$.

One half of the pellets of catalyst $D_1$ is impregnated with a rhodium chloride solution so as to deposit 300 ppm of rhodium. There is thus obtained catalyst $D_2$ of the same composition but further containing 0.03% by weight of rhodium.

CATALYST E₁

⅓ of the powder is impregnated with a solution containing 1 mole of iron nitrate and 0.6 mole of lanthanum nitrate. The remainder of the operation is the same as for catalyst D₁.

The resulting catalyst E₁ has the following relative composition, in % by weight:
Cu=32.4, Co=30.2, Fe=14.3, La=21.3, K=1.8
and by moles: $Cu_1$ $Co_1$ $Fe_{0.5}$ $La_{0.3}$ $K_{0.09}$.

CATALYST F₁

⅓ of the powder is impregnated with a solution containing one mole of ammonium vanadate and 40 g of oxalic acid; the so-impregnated powder is dried for 4 hours at 200° C. and then reimpregnated with a solution containing 0.6 mole of lanthanum nitrate.

After drying for 4 hours at 400° C., heating is performed for 2 hours at 450° C. in the presence of air, and 1.8% by weight of K₂O is deposited.

After activation by heating for 2 hours at 450° C. in air, there is obtained catalyst F₁ having the following relative composition in % by weight:
Cu=32.9, Co=30.5, V=13.2, La=21.6, K=1.8
and by moles: $Cu_1$ $Co_1$ $V_{0.5}$ $La_{0.3}$ $K_{0.09}$.

One half of the pellets of catalyst F₁ is impregnated with a solution of palladium chloride so as to deposit thereon 200 ppm of palladium. There is thus obtained catalyst F₂ having the same composition as F₁ but further containing 0.02% by weight of palladium.

CATALYST G (reference catalyst)

To 4 liters of an aqueous solution, brought to 60° C., of 4 moles of sodium carbonate, there is quickly added 4 liters of an aqueous solution containing 1 mole of copper nitrate, 0.8 mole of cobalt nitrate, 0.4 mole of chromium nitrate, 1 mole of aluminum nitrate and 0.1 mole of barium nitrate.

There is thus obtained a precipitate which is washed several times, dried for 24 hours at 120° C. and then treated for 2 hours at 340° C.

The resulting powder is pelletized to pellets of 5×5 mm.

There is so obtained catalyst G having the following molar composition: $Cr_{0.4}$ $Cu_1$ $Co_{0.8}$ $Al_1$ $Ba_{0.1}$.

CATALYST G₁

The process is conducted in the same manner as for catalyst G, but with the use of 1 mole of copper nitrate, 0.8 mole of cobalt nitrate, 0.2 mole of chromium nitrate, 0.4 mole of aluminum nitrate, 0.8 mole of lanthanum nitrate and 0.1 mole of barium nitrate.

There is thus obtained catalyst G₁, having the following molar composition: $Cr_{0.2}$ $Cu_1$ $Co_{0.8}$ $Al_{0.4}$ $La_{0.8}$ $Ba_{0.1}$.

The activity of the so-prepared catalysts in the synthesis of primary linear alcohols from mixtures of CO, CO₂, H₂ is determined by the amount, expressed in grams per hour and per gram of catalyst, of the different products obtained by passing over the catalysts a gas mixture of the following composition (% by weight):
CO=19
CO₂=13
H₂=66
N₂=2

The temperature is 250° C., the pressure 60 bars and the VVH by volume (N.T.P.) of the reactants per hour and per volume of catalyst is 4000.

The results obtained are reported in the following Table where:

D.M.E. is the abbreviation of dimethyl ether and
CAT is the abbreviation of catalyst.

| CAT | YIELD IN g/h/g CATALYST | | | | | | |
|---|---|---|---|---|---|---|---|
|  | methanol | D.M.E. | ethanol | n.propanol | i.propanol | n.butanol | i.butanol |
| A | 0.076 | 0.001 | 0.125 | 0.063 | 0.006 | 0.045 | 0.001 |
| D | 0.065 | 0.001 | 0.108 | 0.054 | 0.010 | 0.039 | 0.001 |
| E | 0.056 | 0.001 | 0.111 | 0.052 | 0.015 | 0.037 | 0.001 |
| F | 0.063 | 0.008 | 0.104 | 0.030 | 0.08 | 0.029 | 0.001 |
| G | 0.077 | 0.049 | 0.121 | 0.059 | 0.010 | 0.040 | 0.01 |
| B₁ | 0.074 | 0.054 | 0.142 | 0.074 | 0.009 | 0.048 | 0.003 |
| B₂ | 0.087 | 0.009 | 0.149 | 0.081 | 0.007 | 0.051 | 0.001 |
| C | 0.071 | 0.068 | 0.128 | 0.067 | 0.005 | 0.046 | 0.002 |
| D₁ | 0.060 | 0.035 | 0.132 | 0.058 | 0.008 | 0.040 | 0.002 |
| D₂ | 0.079 | 0.010 | 0.135 | 0.063 | 0.007 | 0.041 | 0.002 |
| E₁ | 0.062 | 0.017 | 0.128 | 0.057 | 0.009 | 0.039 | 0.001 |
| F₁ | 0.076 | 0.028 | 0.132 | 0.059 | 0.011 | 0.043 | 0.044 |
| F₂ | 0.084 | 0.011 | 0.141 | 0.061 | 0.012 | 0.049 | 0.005 |
| G₁ | 0.081 | 0.043 | 0.132 | 0.067 | 0.012 | 0.053 | 0.01 |

In all the cases, the selectivity, defined as the molar ratio between (CO+CO₂) converted to alcohols and the total converted (CO+CO₂) is comprised between 90 and 98%.

What is claimed is:

1. In a process for manufacturing saturated linear primary alcohols by contacting a gaseous mixture comprising carbon monoxide and hydrogen, and optionally carbon dioxide, with a multimetallic catalyst having a high selectivity for alcohol production, at a temperature of from 150° to 400° C. and a pressure of from 20 to 250 bar;

the improvement wherein said multimetallic selective catalyst comprises at least five elements, said elements, and the proportion by weight of each element as metal relative to the total weight of said elements as metals, being:
(a) copper, from 20 to 60%;
(b) cobalt, from 5 to 50%;
(c) at least one metal M selected from chromium, iron, vanadium and manganese, from 5 to 30%;
(d) at least one rare earth metal N, from 5 to 40%; and
(e) at least one alkali or alkaline earth metal A, from 0.1 to 5%;
whereby the yield of saturated linear primary alcohols having at least two carbon atoms is increased.

2. A process according to claim 1, wherein the relative proportions by weight are:

copper: 25 to 50%,
cobalt: 10 to 40%,
metal M: 10 to 25%,
metal N: 10 to 30%,
metal A: 0.2 to 3%.

3. A process according to claim 1, wherein zinc is also present in the catalyst composition in a relative proportion of 0.5 to 15% of the total weight of the metals.

4. A process according to claim 1, wherein the catalyst further contains at least one noble metal from group VIII in a relative proportion of from 0.005 to 0.5% of the total weight of the metals.

5. A process according to claim 1, wherein the catalyst further contains one binder selected from alumina, magnesia and cements.

6. A process according to claim 5 wherein the catalyst contains alumina in a proportion of from 1 to 25% by weight, calculated as aluminum.

7. A process according to claim 1, wherein the catalyst contains copper, cobalt, chromium, lanthanum and potassium.

8. A process according to claim 1, wherein the catalyst is prepared by a process comprising the steps of dissolving at least one compound of each of the metals Cu, Co, M and N in water containing a complexant organic compound, followed by evaporating the water, shaping the resultant powder, and impregnating the resultant shaped masses with an aqueous solution of an alkali or alkaline earth metal compound.

9. A process according to claim 8, wherein the complexant compound is selected from the organic polyacids, the alcohol-acids and the amino-acids.

10. A process according to claim 9, wherein the complexant compound is citric acid.

11. A process according to claim 8, wherein, after evaporating the water, the recovered powder is admixed with an aluminous cement, shaped and roasted at 300°–800° C.

12. A process according to claim 1, wherein carbon dioxide is present in the gaseous mixture.

13. A process according to claim 2, wherein the catalyst further contains at least one noble metal from Group VIII in a relative proportion of from 0.005 to 0.5% of the total weight of the metals.

14. A process according to claim 4, wherein said noble metal is platinum, palladium, iridium or rhodium.

15. A process according to claim 14, wherein the proportion of said noble metal is from 0.02 to 0.1%.

16. A process according to claim 7, wherein the catalyst further contains from 0.005 to 0.5% of platinum.

17. A process according to claim 1, wherein the catalyst contains copper, cobalt, chromium, cerium and potassium.

18. A process according to claim 1, wherein the catalyst contains copper, cobalt, manganese, potassium and didymium.

19. A process according to claim 18, wherein the catalyst further contains from 0.005 to 0.5% of rhodium.

20. A process according to claim 1, wherein the catalyst contains copper, cobalt, iron, lanthanum and potassium.

21. A process according to claim 1, wherein the catalyst contains copper, cobalt, vanadium, lanthanum and potassium.

22. A process according to claim 21, wherein the catalyst further contains from 0.005 to 0.5% of palladium.

23. A process according to claim 1, wherein the catalyst contains copper, cobalt, chromium, aluminum, lanthanum and barium.

24. A process according to claim 1, wherein the temperature of the reaction is from 220° to 350° C.

25. A process according to claim 1, wherein the ratio of hydrogen to total carbon monoxide plus carbon dioxide is from 0.4 to 10.

26. A process according to claim 25, wherein said ratio is from 0.5 to 4.

* * * * *